Nov. 7, 1961 L. B. SHERRILL Plant Pat. 2,102

PEACH TREE

Filed July 12, 1960

WITNESS

Addison E. Avery

INVENTOR

Lewis B. Sherrill

Webster & Webster

ATTYS.

United States Patent Office

Plant Pat. 2,102
Patented Nov. 7, 1961

2,102
PEACH TREE

Lewis B. Sherrill, Rte. 2, Box 356, Bakersfield, Calif., assignor of seventy-five percent to Patterson & Hale, Bakersfield, Calif., a partnership Filed July 12, 1960, Ser. No. 42,454
1 Claim. (Cl. 47—62)

This discovery relates to a new and distinct variety of peach tree which bears large clingstone fruit having yellow flesh, and yellow skin overspread to a substantial extent with red.

The present variety, which is a sport of the Redhaven peach (unpatented) has close resemblance thereto in tree growth habit, in appearance of bloom, and in the size, shape, flesh, texture, and exterior color of the fruit; but—in comparison—and as the characteristic feature of novelty—the fruit of the present variety is in harvest approximately ten days earlier.

The present variety is distinctive in comparison with the Garnet Beauty (unpatented), and the Stark Earliglo (United States Plant Patent No. 1,632) in the following particulars:

The large size fruit of the present variety, whose flesh is yellow shading to an orange yellow, is a clingstone whereas the Garnet Beauty is a medium to large size Freestone and the Stark Earliglo a medium size semi-freestone, both with yellow flesh streaked or mottled with red or carmine.

Additionally, the Stark Earliglo is identified by leaves with two to three glands, and fruit having the suture showing on both sides, a short apex, an oval stone irregularly furrowed throughout, and circular pits; the present variety, in contrast, being characterized by leaves with three to five glands, and fruit having the suture showing on one side, a prolonged apex, a globose regularly furrowed stone, and elongated pits.

The instant variety was discovered by me as a limb sport on a Redhaven peach tree growing in an orchard located in the Mettler Station area, Kern County, California. Such orchard is under my supervision and when such limb sport bore fruit its early ripening period, relative to the Redhaven peach, was observed by me and recognized as a distinctive characteristic.

Subsequent to my discovery of the variety I asexually reproduced it—in the aforesaid orchard—by budding over a mature peach tree, as well as a seedling. Such reproductions, now in bearing, ran true to the parent in all repects.

Figure 1:
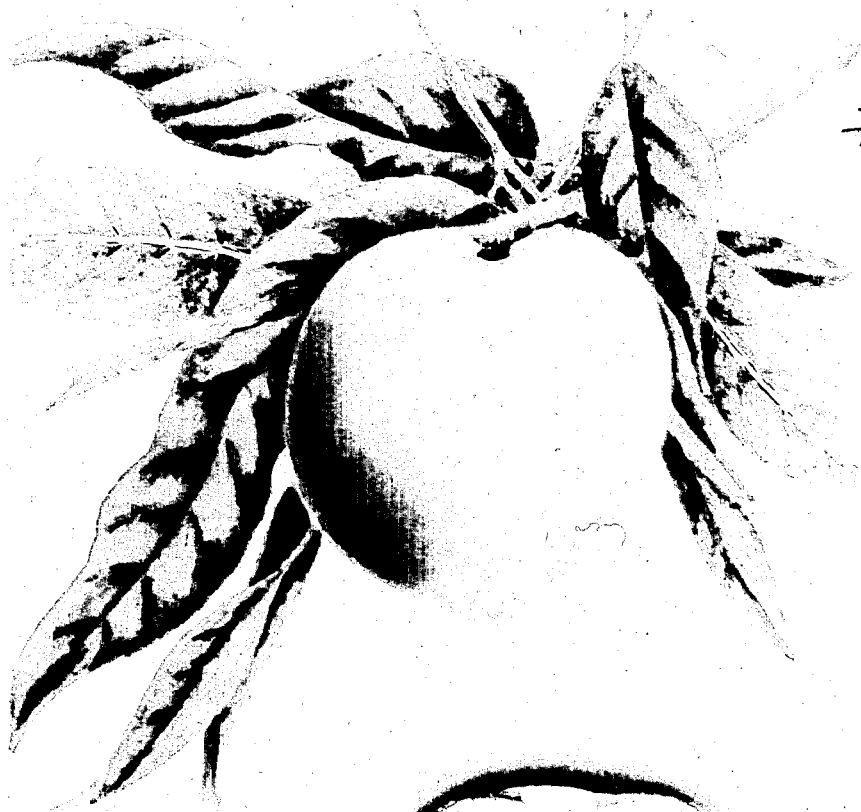
FIG. 1 is an elevation of one of the fruit, together with a twig and leaves.
Figure 2:
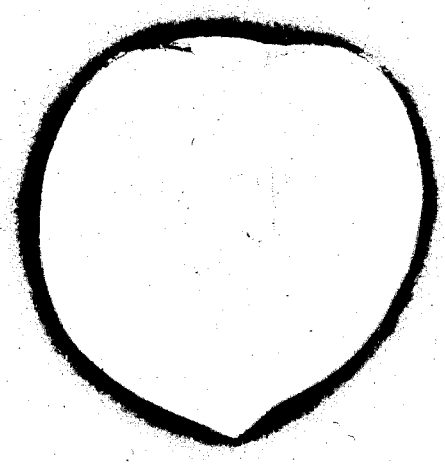
FIG. 2 is a sectional elevation of one of the fruit, but with the cling-type stone remaining wholly in place and shown with the characteristic adherent flesh thereon in part, and removed in part to expose a portion of said stone.

Referring now more specifically to the pomological details of this new and distinct variety of peach tree, the following is an outline description thereof; all major color plate identifications being by reference to Maerz and Paul Dictionary of Color, except where common terms of color definition are employed:

Tree:
- *Size.*—Medium.
- *Vigor.*—Medium.
- *Form.*—Spreading; vase formed.
- *Hardiness.*—Hardy.
- *Production.*—Very productive.
- *Bearing.*—Regular bearer.

Trunk:
- *Size.*—Medium.
- *Bark.*—Medium.

Branches:
- *Size.*—Medium.
- *Bark.*—Medium.
- *Color.*—Brown.
- *Lenticels.*—Number—medium. Size—medium.

Leaves:
- *Size.*—Medium. Average length—5" to 6". Average width—1½" to 2".
- *Form.*—Lanceolate; acutely pointed.
- *Thickness.*—Medium.
- *Surface.*—Smooth.
- *Color.*—Top side—medium green (22–L–7). Under side—lighter green (21–J–6).
- *Margin.*—Finely serrate.
- *Petiole.*—Medium to short length.
- *Glands.*—Average number—three to five. Variable—on petiole at base of blade. Small; mixed.
- *Stipules.*—None.

Flower buds:
- *Hardiness.*—Half-hardy.
- *Size.*—Medium.
- *Length.*—Medium.
- *Form.*—Conic.

Flowers:
- *Blooming period.*—Date of first bloom—March 6, 1960. Date of full bloom—March 16, 1960. Medium as compared with other varieties.
- *Size.*—Medium.
- *Color.*—Salmon.

Fruit:
- *Maturity when described.*—Firm ripe—May 28, 1960.
- *Date of first picking.*—May 28, 1960.
- *Date of last picking.*—June 6, 1960.
- *Size.*—Large; variable. Average diameter axially—3¼". Average transversely in suture plane—3".
- *Form.*—Uniform; symmetrical; globose.
- *Suture.*—Distinct; shallow, extends from base to apex.
- *Ventral surface.*—Rounded.
- *Lips.*—Equal.
- *Cavity.*—Elongated in suture plane, with suture showing on one side. Average depth—⅜".
- *Base.*—Rounded.
- *Apex.*—Prolonged.
- *Pistil point.*—Apical.

Skin:
- *Thickness.*—Medium.
- *Texture.*—Medium.
- *Tenacity to flesh.*—Free.
- *Tendency to crack.*—None.
- *Down.*—Moderate; does not roll up when rubbed.
- *Color.*—Yellow (9–K–3 to 9–K–5) shading to orange yellow (3–H–11), overspread to a substantial extent with red (3–L–5) shading to darker red (7–L–6).

Flesh:
- *Juice.*—Moderate.
- *Texture.*—Firm.
- *Fibers.*—Tender.
- *Ripens.*—Even.
- *Flavor.*—Delicate.
- *Aroma.*—Distinct.
- *Eating quality.*—Best.
- *Color.*—Yellow (9–K–5 to 9–K–8), shading to orange yellow (9–A–8). Surface of pit cavity—yellow.

Stone:

*Type.*—Cling.

*Adherence.*—Adheres to flesh over entire surface.

*Size.*—Medium. Average length—1½". Average breadth—1".

*Form.*—Globose.

*Hilum.*—Oval.

*Sides.*—Equal.

*Surface.*—Regularly furrowed.

*Pits.*—Elongated.

*Tendency to split.*—Slight.

*Color.*—Light tan (10–B–6), with white cast.

Use: Dessert.

Keeping Quality: Good.

Shipping quality: Good.

The tree and its fruit herein described may vary in slight detail due to climatic and soil conditions under which the variety may be grown.

The following is claimed:

A new and distinct variety of peach tree, as illustrated and described, which bears large clingstone fruit having yellow flesh and yellow skin overspread to a substantial extent with red; said variety being a sport of the Redhaven peach and having close resemblance thereto in tree growth habit, in appearance of bloom, and in the size, shape, flesh texture, and exterior color of the fruit; but in comparison—and as the characteristic feature of novelty—the fruit is in harvest approximately ten days earlier; the large size clingstone fruit, whose yellow flesh shades to orange yellow, being in comparison distinct from the medium to large size freestone fruit of the Garnet Beauty and the medium size semi-freestone fruit of the Stark Earliglo, both of the latter having yellow flesh streaked or mottled with red.

References Cited in the file of this patent

Garnet Beauty Variety, originated by Garnet Bruner, described by Brooks and Olma in Proc. Amer. Soc. Hort. Sci. 74: 773, 1959.

Roxburgh (Stark Earliglo Variety), Plant Patent 1,632, August 13, 1957.